United States Patent
Blaney

(10) Patent No.: US 6,346,097 B1
(45) Date of Patent: *Feb. 12, 2002

(54) PERSONAL CARE PRODUCT WITH EXPANDABLE BM CONTAINMENT

(75) Inventor: Carol Ann Blaney, Roswell, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/908,886

(22) Filed: Aug. 8, 1997

(51) Int. Cl.$^7$ .................. A61F 13/15; A61F 13/20; A61M 1/00

(52) U.S. Cl. .................. 604/327; 604/369; 604/374; 604/378; 604/379; 604/385.01; 604/385.19

(58) Field of Search ................ 604/348, 369, 604/377–382, 385.1, 385.2, 393–396, 374, 388.01, 385.12, 385.14, 385.19, 385.03–385.05, 387, 327

(56) References Cited

U.S. PATENT DOCUMENTS

| | | |
|---|---|---|
| 1,833,960 A | 12/1931 | Alsop |
| 1,971,671 A | 8/1934 | Alsop |
| 2,004,088 A | 6/1935 | Alsop |
| 2,069,092 A | 1/1937 | Jackson, Jr. |
| 2,837,095 A | 6/1958 | Stevenson |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,570,493 A * | 3/1971 | Olsson ............. 604/369 |
| 3,572,392 A * | 3/1971 | Lindquist et al. ...... 604/369 |
| 3,626,943 A * | 12/1971 | Worcester ............ 604/348 |
| 3,653,382 A * | 4/1972 | Easley et al. ......... 604/369 |
| 3,692,618 A | 9/1972 | Dorschner et al. |
| 3,736,931 A * | 6/1973 | Glassman ............ 604/372 |
| 3,802,817 A | 4/1974 | Matsuki et al. |
| 3,849,241 A | 11/1974 | Butin et al. |
| 4,041,950 A * | 8/1977 | Jones, Sr. ........... 604/318.1 |
| 4,100,324 A | 7/1978 | Anderson et al. |
| 4,116,197 A | 9/1978 | Bermingham |
| 4,340,563 A | 7/1982 | Appel et al. |
| 4,413,996 A | 11/1983 | Taylor |
| 4,560,372 A * | 12/1985 | Pieniak ............. 604/369 |
| 4,560,380 A | 12/1985 | Tharel |
| 4,662,877 A | 5/1987 | Williams |
| 4,676,785 A * | 6/1987 | Battista ............. 604/369 |
| 4,681,577 A * | 7/1987 | Stern et al. .......... 604/385.19 |
| 4,731,071 A | 3/1988 | Pigneul |
| 4,753,645 A | 6/1988 | Johnson |

(List continued on next page.)

FOREIGN PATENT DOCUMENTS

| | | | |
|---|---|---|---|
| EP | 0 486 006 | 5/1992 | |
| EP | 0 644 748 | 12/1997 | |
| WO | 9108722 | * 6/1991 | ............. 601/393 |
| WO | 95/05139 | 2/1995 | |
| WO | 96/40029 | 12/1996 | |
| WO | 97/01998 | 1/1997 | |

Primary Examiner—John G. Weiss
Assistant Examiner—K. M. Reichle
(74) Attorney, Agent, or Firm—James B. Robinson

(57) ABSTRACT

There is provided a BM containment system for personal care products having an expandable material which expands upon contact with fluids to form a compartment in which BM may be contained. The system may optionally have a dewatering layer on the side away from a wearer of the personal care product. The system may also be in liquid isolation from other personal care product components which are located on the side away from a wearer in order to keep the BM containment system from expanding from exposure to urine. Liquid isolation may be provided by a film between the other system components and the traditional personal care product components.

8 Claims, 8 Drawing Sheets

U.S. PATENT DOCUMENTS

| | | |
|---|---|---|
| 4,778,459 A | 10/1988 | Fuisz |
| 4,781,711 A | 11/1988 | Houghton et al. |
| 4,787,896 A | 11/1988 | Houghton et al. |
| 4,818,464 A | 4/1989 | Lau |
| 4,892,536 A | 1/1990 | DesMarais et al. |
| 4,990,147 A | 2/1991 | Freeland |
| 4,994,052 A * | 2/1991 | Kimura .................. 604/385.1 |
| 5,048,589 A | 9/1991 | Cook et al. |
| 5,062,840 A | 11/1991 | Holt et al. |
| 5,108,827 A | 4/1992 | Gessner |
| 5,147,345 A * | 9/1992 | Young et al. |
| 5,176,672 A | 1/1993 | Bruemmer et al. |
| 5,207,663 A | 5/1993 | McQueen |
| 5,269,775 A | 12/1993 | Freeland et al. |
| 5,277,976 A | 1/1994 | Hogle et al. |
| 5,342,583 A * | 8/1994 | Son ............................ 604/393 |
| 5,348,620 A | 9/1994 | Hermans et al. |
| 5,382,400 A | 1/1995 | Pike et al. |
| 5,387,207 A | 2/1995 | Dyer et al. |
| 5,397,316 A * | 3/1995 | LaVon et al. |
| 5,399,412 A * | 3/1995 | Sudall et al. |
| 5,514,121 A * | 5/1996 | Roe et al. |
| 5,520,674 A * | 5/1996 | Lavon et al. |
| 5,527,302 A * | 6/1996 | Endres et al. |
| 5,607,416 A * | 3/1997 | Yamamoto et al. |
| 5,624,423 A * | 4/1997 | Anjur ......................... 604/367 |
| 5,676,661 A * | 10/1997 | Faulks .................... 604/385.1 |
| 6,120,485 A * | 9/2000 | Gustafsson et al. ...... 604/385.3 |
| 6,133,501 A * | 10/2000 | Hallock et al. ........ 604/385.19 |

* cited by examiner

PERSONAL CARE PRODUCT WITH EXPANDABLE BM CONTAINMENT

FIELD OF THE INVENTION

The present invention relates to the field of incontinence management, specifically BM incontinence, and the associated personal care products such as diapers, training pants, adult incontinence products and the like.

BACKGROUND OF THE INVENTION

Personal care products have evolved considerably in the area of preventing urine leakage, but little has been done to address the concern of BM leakage which is often a much more inconvenient problem than urine leakage.

Both urine and BM leakage have been addressed with features such as leg cuffs which appear to reduce leg BM leakage somewhat. If sufficient void volume does not exist to contain the BM within the product, however, this fluid will escape out the back or front of the product, or even over the side of the leg cuff and out the leg opening. Even the best leg cuff design cannot contain BM where there is insufficient void volume in the product to contain it. Hence, one problem that remains is that of providing the necessary void volume inside a personal care product to contain the BM.

Another need related to the issue of BM containment is the need to keep the personal care product volume very low prior to use. Modern packaging techniques significantly compress the products, e.g. diapers, so that transportation costs, shelf space, storage space required of the consumer, etc., are minimized. A successful BM containment device or system must keep the pre-use volume of personal care products low.

Further, it is well known that BM contacting the skin is a major factor influencing diaper rash due to enzymatic irritants in the BM. This detrimental effect is made more severe when these irritants interact with urine. Minimizing contact of BM with the skin, and minimizing intermixing of the BM with urine are two skin-health benefits a BM containment system should address and are objects of this invention.

Finally, a BM containment system should provide a visual signal that the personal care product has been insulted with BM, alerting the caretaker of the need to change the product.

It is an object of this invention, therefore, to provide a BM (feces) containment system for personal care products which keeps the product pre-use volume low. It is a further object of this invention to provide sufficient void volume within the product in which to contain BM in order to reduce the possibility of BM leakage outside the product. It is a further object of this invention to provide a visual signal that a personal care product with the BM containment system of this invention has been insulted. It is a further object of this invention to minimize contact of BM with the skin, as well as minimize intermixing of the BM with the urine.

SUMMARY OF THE INVENTION

The objects of this invention are achieved by a BM containment system for personal care products having an expandable material which expands upon contact with fluids to form a compartment in which BM may be contained. The BM containment system may optionally have a dewatering layer on the side away from a wearer of the personal care product. The system is in liquid isolation from other personal care product components (which are located on the side away from a wearer) in order to keep the BM containment system from expanding from exposure to urine. Liquid isolation may be provided by a film between the other system components and the traditional personal care product components.

DEFINITIONS

Figure 1:
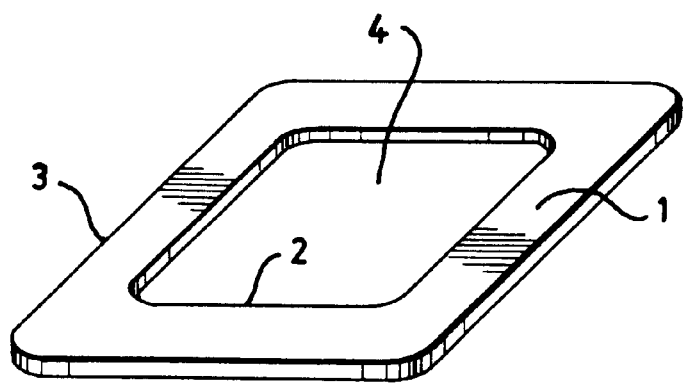
FIG. 1 is a drawing of a view of an expandable material in a compressed or pre-expanded configuration.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Layer" when used in the singular can have the dual meaning of a single element or a plurality of elements.

"Liquid" means a nongaseous, nonparticulate substance and/or material that flows and can assume the interior shape of a container into which it is poured or placed.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns, (Note that to convert from osy to gsm, multiply osy by 33.91).

As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

"Spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns.

"Meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

As used herein, the term "coform" means a process in which at least one meltblown diehead is arranged near a chute through which other materials are added to the web while it is forming. Such other materials may be wood pulp, superabsorbent particles, cellulose or staple fibers, for example. Coform processes are shown in commonly assigned U.S. Pat. Nos. 4,818,464 to Lau and 4,100,324 to Anderson et al. Webs produced by the coform process are generally referred to as coform materials.

"Conjugate fibers" refers to fibers which have been formed from at least two polymer sources extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught, for example, in U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. No. 5,277,976 to Hogle et al. which describes fibers with unconventional shapes.

"Biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner.

"Bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

"Airlaying" is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive.

As used herein "uncreped through-air dried" or UCTAD refers to a process of making a material, and to the material made thereby, by forming a furnish of cellulosic fibers, depositing the furnish on a traveling foraminous belt, subjecting the fibrous web to non-compressive drying to remove the water from the fibrous web, and removing the dried fibrous web from the traveling foraminous belt. Such webs are described in U.S. Pat. Nos. 5,048,589, 5,348,620 and 5,399,412.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, through-air bonding means a process of bonding a fiber web in which air which is sufficiently hot to melt the polymers of which the fibers of the web are made is forced through the web. The air velocity is between 100 and 500 feet per minute and the dwell time may be as long as 6 seconds. The melting and resolidification of the polymer provides the bonding.

"Personal care product" means diapers, training pants, absorbent underpants, feminine hygiene products and adult incontinence products.

DETAILED DESCRIPTION

The present invention is a new component in a personal care product like a diaper or similar incontinent product which is termed the "BM compartment". The BM compartment resides adjacent to the anal opening and serves to take in BM, dewater it, and contain it, while providing void volume on demand for containing the BM. Certain embodiments of the BM compartment also prevent urine from entering into the compartment, thus segregating the BM from the urine. The BM compartment, due to its function of collecting and containing the BM, serves to minimize skin contact with the BM by preventing the spread of BM outside the BM compartment. Leakage is minimized by (1) providing void volume to contain the BM inside the diaper or similar product, and (2) containing the BM within the BM compartments perimeter, which lies inside the product. Finally, the BM compartment in an expanded configuration provides a visual cue to the caretaker that it is time to change the product.

Turning to the drawings, FIG. 1 shows the simplest configuration of the BM containment system of this invention whereby an expandable material (1) is provided which has an inner edge (2) and an outer edge (3). The inner edge (2) defines an open or void area (4) which, upon expansion of the expandable material after contact with liquid in a personal care product, will become a compartment for the storage of BM. The top or wearer side of the BM containment system will be positioned adjacent the anal area of a wearer, also called the BM target zone. The bottom side, the side away from the personal care product wearer, will be in contact with the remainder of the personal care product to which it may be secured by known means such as adhesive bonding.

Figure 2:
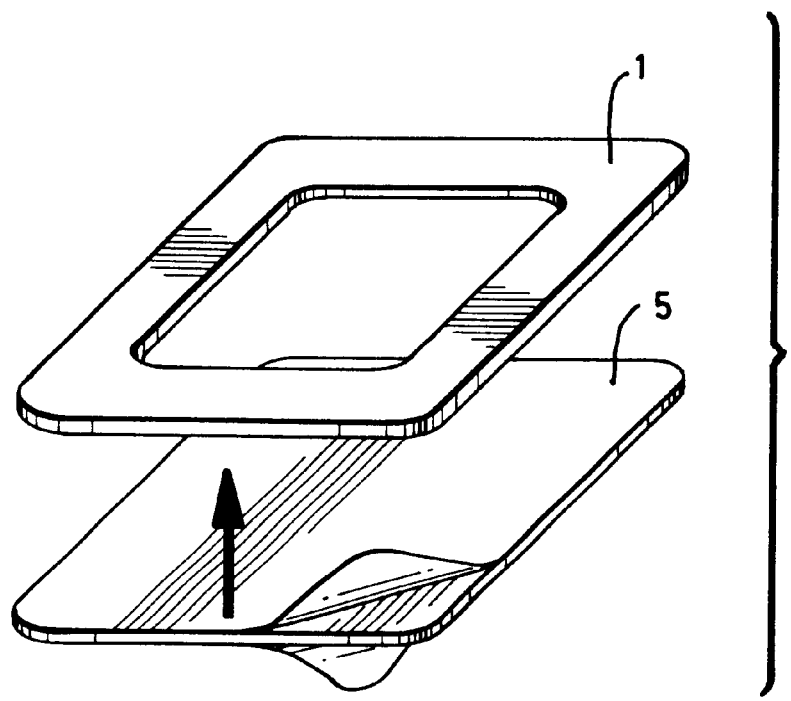
FIG. 2 is a drawing of a view of an expandable material in a compressed or pre-expanded configuration and having a BM dewatering layer on the side away from the wearer.

FIG. 2 shows the material of FIG. 1 to which has been added a BM dewatering material (5) on the bottom lower side. The BM dewatering material may be, for example, an uncreped through air dried tissue, or other material capable of absorbing liquid from the BM.

Figure 3:
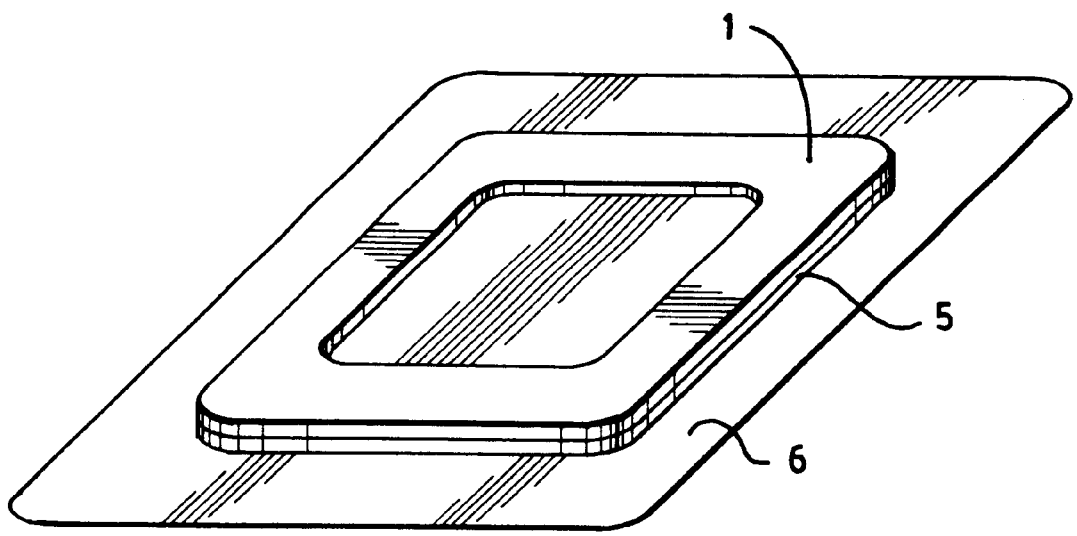
FIG. 3 is a drawing of a view of an expandable material in a compressed or pre-expanded configuration, having a BM dewatering layer on the side away from the wearer and having a barrier layer next to the dewatering layer.

FIG. 3 shows the configuration of FIG. 2 to which has been added a barrier layer (6) below the dewatering material (5). The barrier layer (6) serves to isolate the BM containment system from liquid from the rest of the personal care product so that other waste streams, e.g. urine, do not prematurely expand the expandable material (1). The barrier layer (6) may be made from anything which can isolate the BM containment system from liquid from the rest of the personal care product, such as films, nonwoven fabrics and a latex coating applied to the dewatering material (5), etc.

Figure 4:
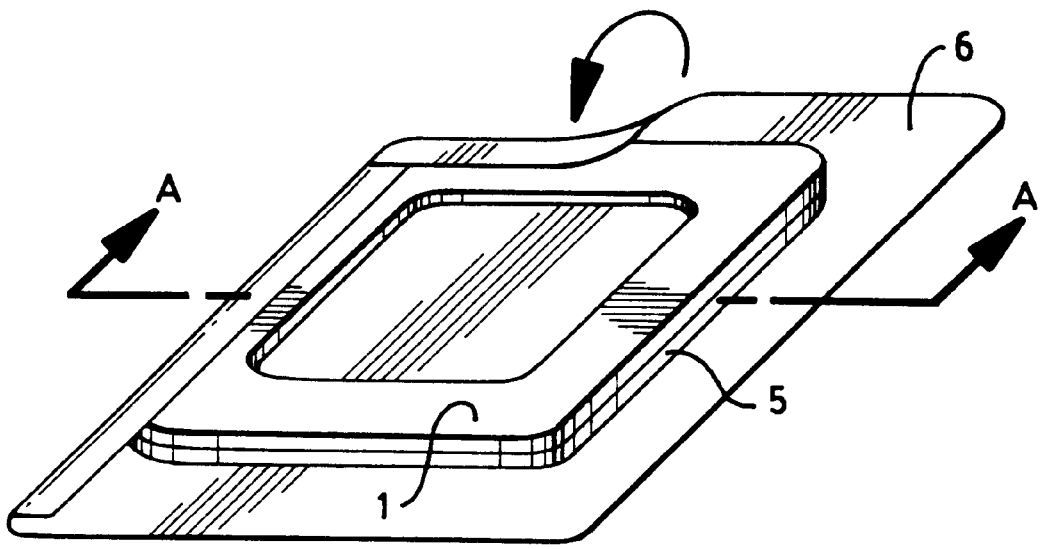
FIG. 4 is a drawing of the view of FIG. 3 wherein the barrier layer is folded around the edge of the expandable material so that it comes in contact with the top (wearer side) of the expandable material.

FIG. 4 shows the BM containment system of FIG. 3 where the barrier layer (6) is a nonwoven fabric or film which is folded around and over the expandable material (1) and the dewatering material (5).

Figure 5A:
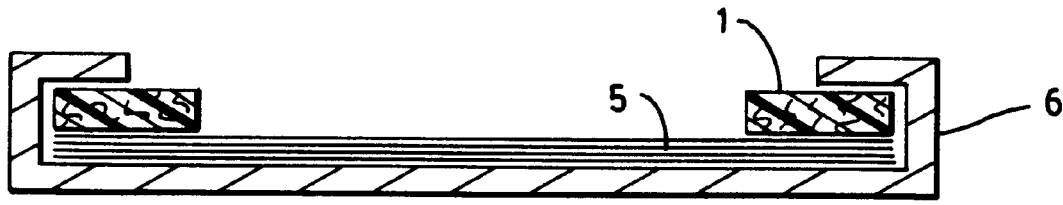
FIG. 5 shows a before (5a) and after (5b) view of the expandable material configuration shown in FIG. 4.
In FIG. 5b the expandable material has expanded after contact with BM.
Figure 5B:
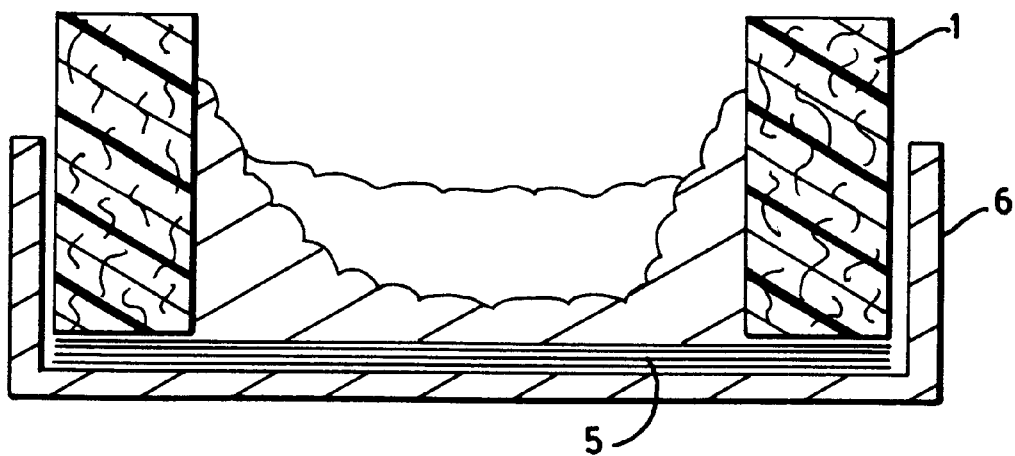

FIGS. 5a and 5b are cross-sectional views of the BM containment system of FIG. 4 along section line A—A. FIG. 5a shows the system before an insult where the expandable material (1) is adjacent a dewatering material (5) which is adjacent a barrier layer (6) which also folds up and around the expandable material (1). FIG. 5b shows the same cross-sectional view after a BM insult. The expandable material (1) has expanded, causing the portion of the barrier layer (6) which was on top of the expandable material (1) to be moved out of the way.

Figure 6:
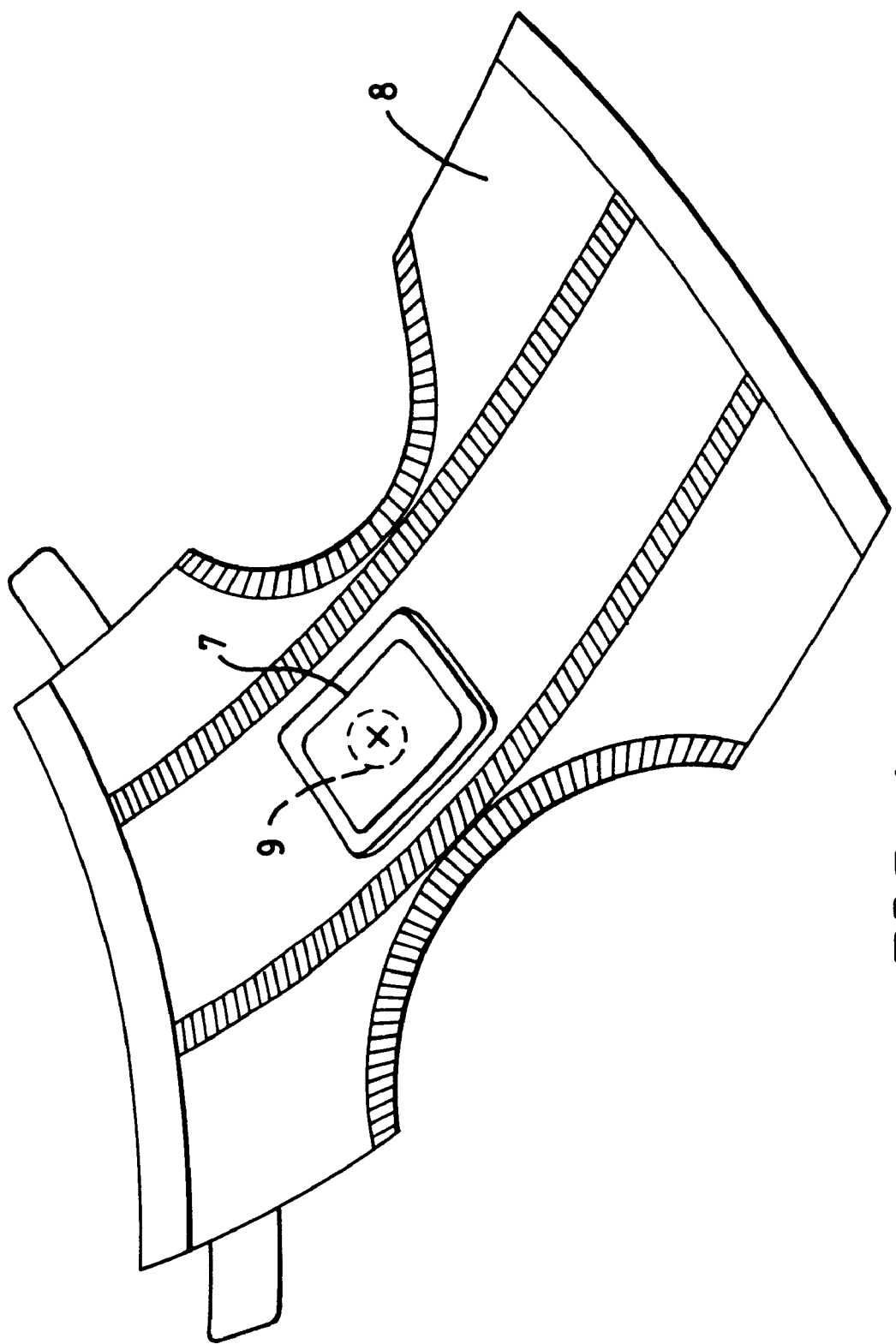
FIG. 6 shows a diaper having the BM containment system of this invention located in the anal area or BM target zone.

FIG. 6 shows the a BM containment system (7) as it may appear in a diaper (8). The system (7) is positioned in the anal area or BM target zone (9) which is in the back of the diaper (8).

Figure 7:
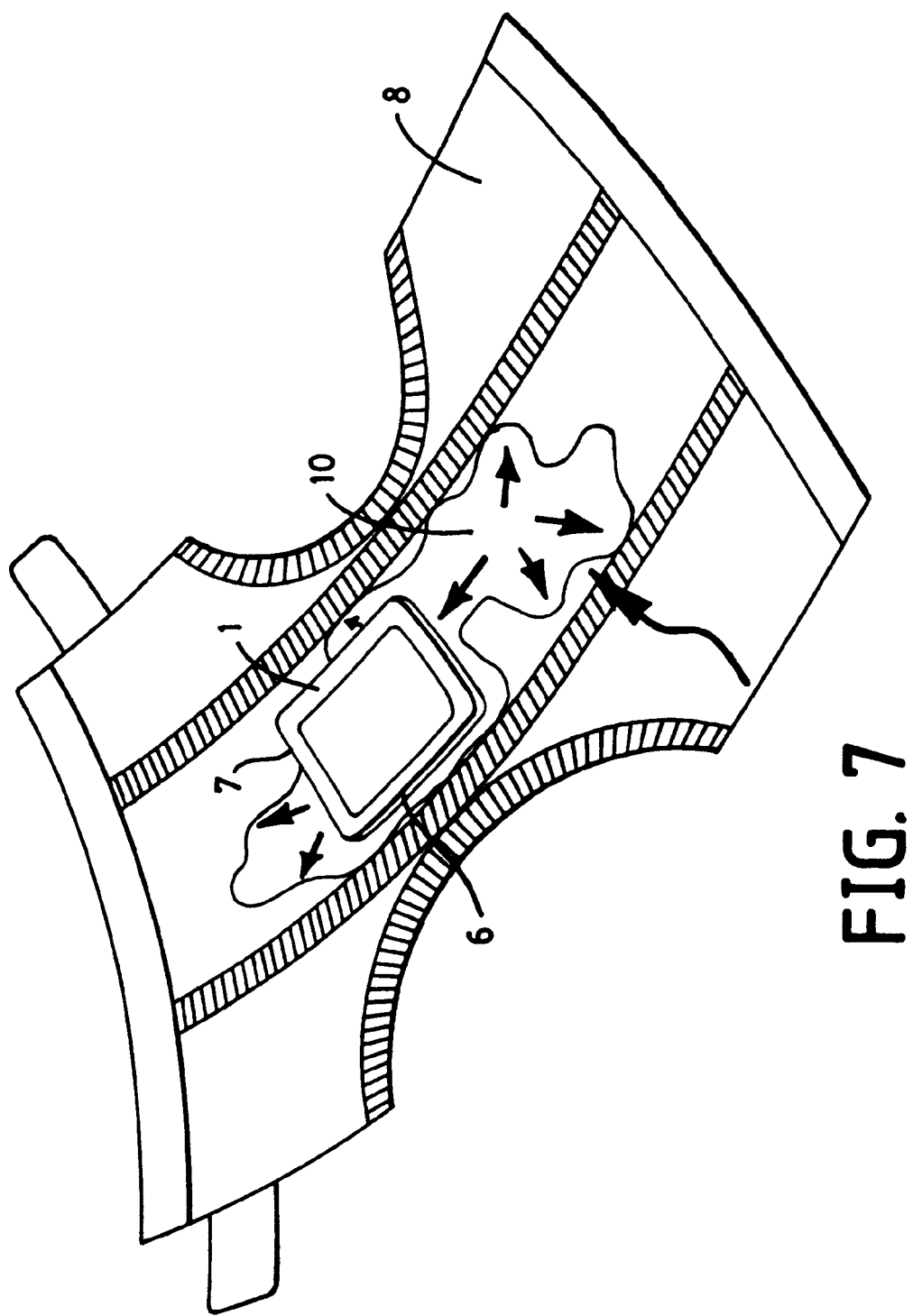
FIG. 7 shows the diaper of FIG. 6 after an insult of urine where the arrows show the direction of travel of the urine.

FIG. 7 illustrates the configuration of FIG. 6 upon an insult by urine only. The arrows indicate the movement of urine away from the urine target zone (10). The barrier layer (6) keeps urine from reaching the expandable material (1) yet does not prevent urine from spreading below the system (7) and so more efficiently using the absorbents present in traditional diapers.

Figure 8:
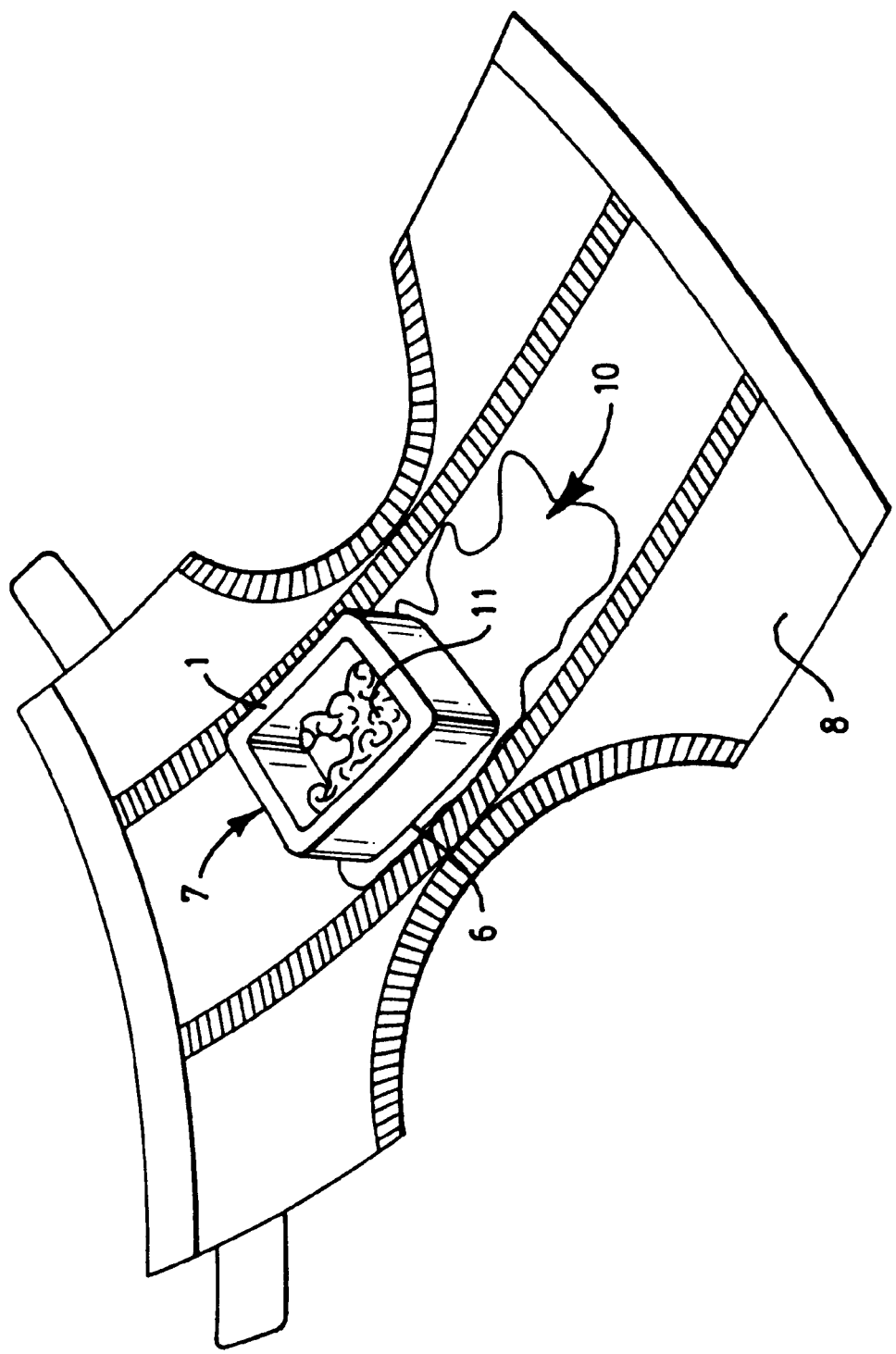
FIG. 8 shows a diaper having the BM containment system which has been insulted by both urine and BM. The expandable material has expanded and formed a compartment for containment of the BM.

FIG. 8 shows the configuration of FIG. 6 after a urine insult, as shown in FIG. 7, and after a BM insult. The expandable material (1) has expanded to produce a compartment (11) which provides void volume to keep the BM from being pushed out of the diaper (8). Expansion has been caused by liquid in the BM, not from urine, as the barrier layer (6) maintains the system (7) in liquid isolation from the other liquid containing layers of the diaper (8).

Figure 9:
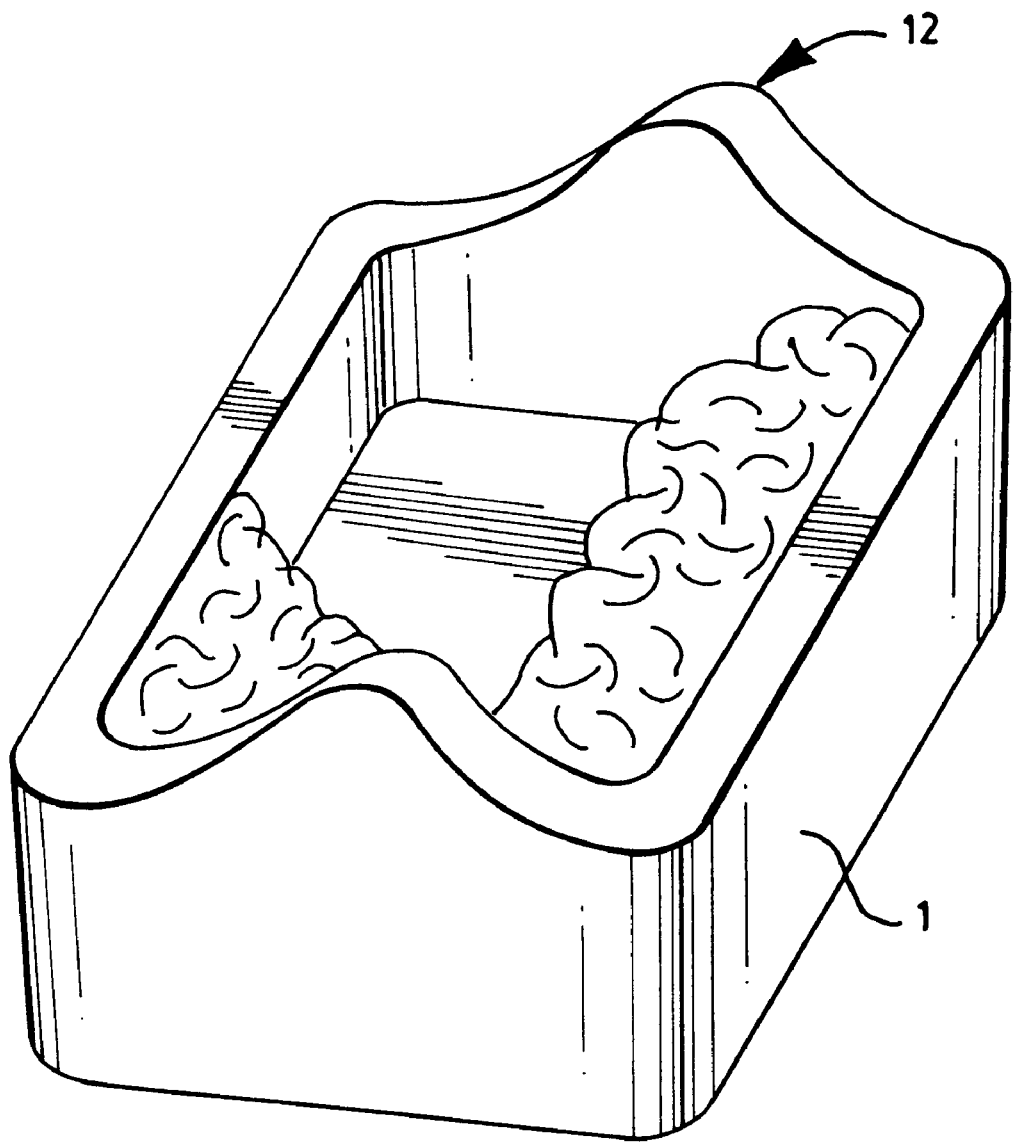
FIG. 9 shows a view of an expandable material for BM containment whereby the expandable material has an expanded shape which provides a gluteal ridge seal.
Figure 10:
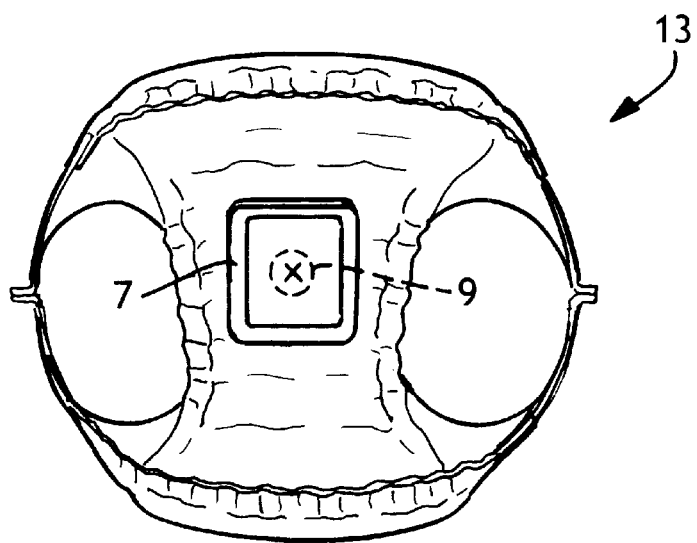
FIG. 10 shows a training pant which may use the BM containment system of the invention.
Figure 11:
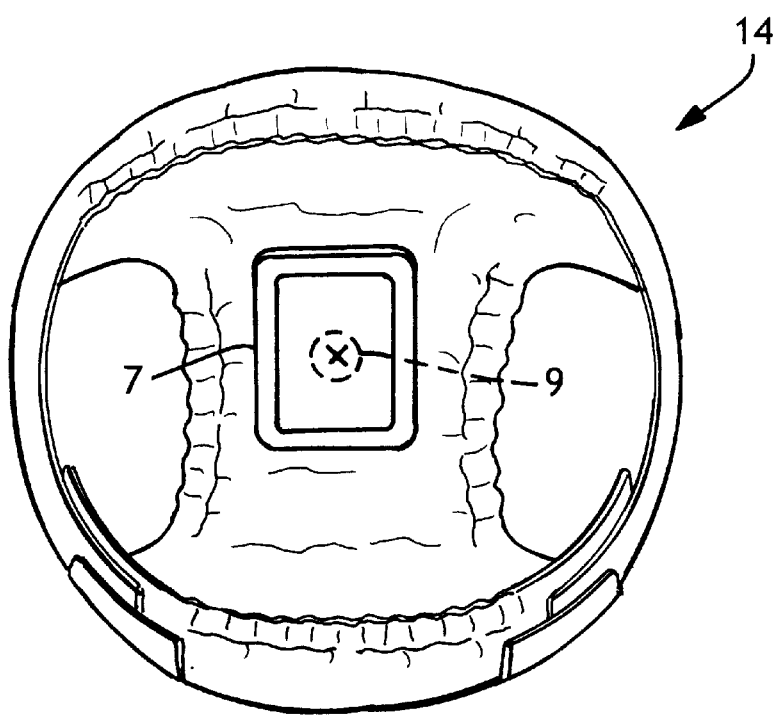
FIG. 11 shows an adult incontinence article which may use the BM containment system of the invention.

FIG. 9 shows another embodiment of any of FIGS. 1 through 4 where the expandable material (1) is provided with a gluteal ridge seal (12) which is quite visible when the material is expanded.

Various materials may be used to assemble a BM Compartment. The first is an expandable material which expands upon contact with water. One example of such a material is compressed cellulosic foam such as that sold by Industrial Commercial Supply Inc., of Akron Ohio as COMPRESSED CELLULOSE SHEETS. For example, a one-inch square of compressed cellulosic foam approximately $\frac{1}{16}$ inch thick, when wetted with water, expands to a 1" cube in a matter of about a second. Other materials may include expandable fibrous mats like those made from bonded carded webs or conjugate fiber spunbond webs that have been compressed and retain their compressed shape via a water soluble adhesive or other bonding means. Coform materials as described above and foams such as described in U.S. Pat. No. 5,387,207 to Dyer et al. and U.S. Pat. No. 5,397,316 to LaVon et al. may also function in this invention. It is important that whatever material used for the expandable portion of this invention expand rapidly to a size many times its original size upon being wetted. This means that the material should expand to at least four times its initial thickness in a matter of at most 60 seconds.

The expandable material is selected from the group consisting of compressed cellulose, foam, coform materials, fibrous mats, and mixtures thereof.

The optional BM dewatering material may be an uncreped through-air-dried tissue (UCTAD).

The barrier layer may be a body fluid-impermeable material such as a polyolefin film or nonwettable (hydrophobic) meltblown nonwoven fabric. Particularly well suited in terms of function and cost is polyethylene film.

EXAMPLE

One method of constructing a BM containment system is to cut a perimeter of expandable foam or cellulosic material as shown in FIG. 1. The perimeter has an outer perimeter edge, and inner perimeter edge, and an opening or hole in the middle. In this Example the BM containment system was made from compressed cellulose sheets cut into a size of 6.35 cm (2.5 inches) in width, 7.62 cm (3 inches) in length and 0.32 cm (⅛ inch) in height prior to insult. The opening or hole for the compartment was 4.45 cm (1.75 inches) by 5.72 cm (2.25 inches). This Example contained about 3.5 gms of cellulose at a density of 0.43 g/cc before expansion and 0.034 g/cc (dry) after expansion. It should be noted that other sizes for the materials would also work depending on the size of the wearer. The material serves as the expandable 'fence' which expands upon contact with BM, thus serving to provide a void volume to contain the BM.

The optional dewatering material may be cut in the same shape as the outer perimeter of the 'fence'. The fence should be set on top of the dewatering material as shown in FIG. 2.

Lastly, a piece of the fluid-impermeable barrier material may be cut in the same general shape as the 'fence' but with a larger perimeter to allow extra edging to fold up over the sides of the expandable material as illustrated in FIG. 3. The barrier layer may be attached to the expandable material with adhesive, ultrasonic bonding, stitching, or other means. A water-soluble adhesive (e.g. starchbased) serves the additional advantage of releasing the expanding material when wetted. In this case, the various materials were bonded together by adhesive tape. FIG. 4 shows how the barrier material may be wrapped around the other two components.

The BM containment system of this invention is placed on the wearer side of a personal care product like a diaper, adjacent to the anal opening as shown in FIG. 6. The system may be adhered with hook and loop type fasteners like VELCRO fasteners, adhesive, ultrasonic bonding, or other known bonding means. It may be placed by a diaper manufacturer or by the caretaker, which may allow for more accurately locating the system adjacent the BM target zone. When urine insults the diaper, urine is taken in and wicks throughout the diaper in a similar fashion to a conventional diaper, e.g. around and underneath the BM compartment having a barrier layer, as shown in FIG. 7. The urine does not cause the BM compartment to expand since the barrier material around the BM compartment prevents urine from entering it.

When BM strikes the BM compartment, however, the BM's moisture causes the expandable material to expand, thus forming a 'fence' around the BM to contain it and provide an expanded void volume of at least about 10 cc. At the same time, the BM dewatering material, if used, dewaters the BM further, increasing its viscosity and further acting to inhibit BM movement out of the designated BM compartment. This is illustrated in FIG. 8.

A lab test of the BM containment system described in the Example above was performed by placing it into a HUGGIES SUPREME diaper, step 3 at the BM target zone and insulting it with synthetic urine (0.875 weight percent NaCI saline solution) onto the urine target zone. Over 400 ml of saline were added at the urine target zone and the BM compartment was not affected. The saline was taken into the diaper under and beyond the BM compartment. That is, the BM compartment was not detrimental to urine uptake and distribution. Next, to mimic runny BM, about 10 ml saline fluid was poured into the BM compartment, onto the anal area or BM target zone, and it immediately caused the perimeter to expand, providing void volume and containment of the fluid, and segregating it from the earlier saline insult which went into the urine target zone.

As can be seen from the above description, there is herein provided a BM containment compartment which can take in BM, dewater it, and contain it, while providing void volume on demand for containing the BM. The BM compartment also prevents urine from entering into it, thus segregating the BM from the urine. The BM compartment, due to it's function of collecting and isolating the BM, serves to minimize skin contact with the BM by preventing the spread of BM outside the BM compartment. Finally, the BM compartment in an expanded configuration provides a visual cue to the caretaker that it is time to change the product. This provides a great advance in personal care product design.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A diaper comprising a urine target zone, and a BM containment system, wherein said BM containment system comprises an annular expandable material which expands upon contact with fluids to form a compartment adapted for positioning adjacent to an anal opening in which BM may be contained, and wherein said BM containment system further comprises barrier means adjacent and below said compartment to isolate said compartment from urine from the target zone.

2. The diaper of claim 1 further comprising a dewatering layer between said BM containment system and said barrier means.

3. The diaper of claim 1 wherein said expandable material is selected from the group consisting of compressed cellulose, foam, coform materials, fibrous mats, and mixtures thereof.

4. The diaper of claim 1 wherein said BM containment system further comprises a gluteal ridge seal.

5. A training pant comprising a urine target zone, and a BM containment system, wherein said BM containment system comprises an expandable material having a void defined therein, which material expands upon contact with fluids to form a compartment adapted for positioning adjacent to an anal opening and which accepts and contains BM, and said BM containment system further comprising a barrier selected from the group consisting of films and nonwoven fabrics adjacent and below said compartment which isolates said compartment from urine from the target zone.

6. The training pant of claim 5 which further comprises a dewatering material between said compartment and said barrier.

7. The training pant of claim 5 wherein said barrier is film comprised of polyethylene.

8. An adult incontinence product comprising a urine target zone, and a BM containment system, wherein said BM containment system comprises;

an annular expandable material having an inner edge and an outer edge, wherein said inner edge defines a void, which material expands upon contact with fluids to form a compartment adapted for positioning adjacent to an anal opening and which accepts and contains BM;

a dewatering material adjacent said expandable material, on a side adapted for positioning away from a wearer, and;

a polyethylene film adjacent said dewatering material on the side adapted for positioning away from the wearer to isolate said dewatering material and said expandable material from urine from the target zone.

* * * * *